US010188359B2

(12) United States Patent
Kim et al.

(10) Patent No.: US 10,188,359 B2
(45) Date of Patent: Jan. 29, 2019

(54) INTRA-ORAL SENSOR, CRADLE, AND INTRA-ORAL SENSING SYSTEM

(71) Applicants: Rayence Co., Ltd., Gyeonggi-do (KR); VATECH EWOO Holdings Co., Ltd., Gyeonggi-do (KR)

(72) Inventors: Keun Young Kim, Gyeonggi-do (KR); Tae Woo Kim, Gyeonggi-do (KR); Sung Il Choi, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 140 days.

(21) Appl. No.: 15/127,837

(22) PCT Filed: Mar. 23, 2015

(86) PCT No.: PCT/KR2015/002839
§ 371 (c)(1),
(2) Date: Sep. 21, 2016

(87) PCT Pub. No.: WO2015/142146
PCT Pub. Date: Sep. 24, 2015

(65) Prior Publication Data
US 2017/0086760 A1  Mar. 30, 2017

(30) Foreign Application Priority Data

Mar. 21, 2014 (KR) ........................ 10-2014-0033227

(51) Int. Cl.
*H01J 31/49* (2006.01)
*A61B 6/14* (2006.01)
(Continued)

(52) U.S. Cl.
CPC ............ *A61B 6/145* (2013.01); *A61B 6/4423* (2013.01); *A61B 6/56* (2013.01); *A61C 9/004* (2013.01);
(Continued)

(58) Field of Classification Search
CPC .. A61B 6/00; A61B 6/14; A61B 6/145; A61B 6/4423; A61B 6/56;
(Continued)

(56) References Cited

U.S. PATENT DOCUMENTS 6,030,119 A   2/2000  Tachibana et al.
6,307,915 B1  10/2001 Frojdh
(Continued)

FOREIGN PATENT DOCUMENTS

JP  2003-079617 A  3/2003
JP  2006-043465 A  2/2006
WO    96/03917 A1  2/1996

OTHER PUBLICATIONS

Korean Intellectual Property Office, International Search Report of International Application No. PCT/KR2015/002839, dated Jul. 27, 2015.
(Continued)

*Primary Examiner* — Jurie Yun
(74) *Attorney, Agent, or Firm* — IP Legal Services, LLC

(57) ABSTRACT

Disclosed are an intra-oral sensor, a cradle, and an intra-oral sensing system. More particularly, the present invention relates to an intra-oral sensor, a cradle, and an intra-oral sensing system, in which the intra-oral sensor can transmit projection data, can be charged with driving power, and can be sterilized at the same time when mounting the intra-oral sensor in the cradle, and can output the projection data including an identifier therein, thereby enabling an operator
(Continued)

to easily recognize which part in a set of teeth is represented by image data corresponding to the projection data.

5 Claims, 4 Drawing Sheets

(51) Int. Cl.
    *A61C 9/00*     (2006.01)
    *A61B 6/00*     (2006.01)
    *A61L 2/10*     (2006.01)

(52) U.S. Cl.
    CPC ......... *A61L 2/10* (2013.01); *A61B 2560/0456* (2013.01); *A61L 2202/24* (2013.01)

(58) Field of Classification Search
    CPC ............... A61B 2560/0456; A61L 2/10; A61L 2202/24; G03B 42/04; G03B 42/042
    USPC ............... 378/98.8, 168, 169, 189, 191, 204
    See application file for complete search history.

(56) References Cited

U.S. PATENT DOCUMENTS

| | | |
|---|---|---|
| 6,320,934 B1 | 11/2001 | Carroll et al. |
| 6,404,854 B1 | 6/2002 | Carroll et al. |
| 2001/0055368 A1 | 12/2001 | Carroll |
| 2006/0028546 A1 | 2/2006 | Kokkaliaris et al. |
| 2007/0053498 A1 | 3/2007 | Stan Mandelkem et al. |
| 2007/0286335 A1 | 12/2007 | De Godzinsky |

OTHER PUBLICATIONS

Korean Intellectual Property Office, Written Opinion of the International Searching Authority of International Application No. PCT/KR2015/002839, dated Jul. 27, 2015.

European Patent Office, Extended European Search Report of corresponding EP Patent Application No. 15764895.7, dated Nov. 28, 2017.

INTRA-ORAL SENSOR, CRADLE, AND INTRA-ORAL SENSING SYSTEM

CROSS REFERENCE TO RELATED APPLICATIONS

This application is a National Stage Patent Application of PCT International Patent Application No. PCT/KR2015/002839 (filed on Mar. 23, 2015) under 35 U.S.C. § 371, which claims priority to Korean Patent Application No. 10-2014-0033227 (filed on Mar. 21, 2014), the teachings of which are incorporated herein in their entireties by reference.

TECHNICAL FIELD

The present invention relates generally to an intra-oral sensor, a cradle, and an intra-oral sensing system. More particularly, the present invention relates to an intra-oral sensor, a cradle, and an intra-oral sensing system, in which the intra-oral sensor can transmit projection data, can be charged with driving power, and sterilized at the same time when mounting the intra-oral sensor in the cradle, and can output the projection data including an identifier therein, thereby enabling an operator to easily recognize which part in a set of teeth is represented by image data corresponding to the projection data.

BACKGROUND ART

In general, intraoral radiography is performed to obtain information about teeth in the oral cavity of a patient in a dental clinic, etc. Further, intraoral radiography is performed by placing an intra-oral sensor in the oral cavity of the patient and projecting X-rays from an external radiography device onto the oral cavity of the patient.

Further, in the related art, an intra-oral sensor is referred to as an oral sensor, and is configured to include: a sensing unit that generates an electrical signal in accordance with radiation decrement of X-rays projected onto the oral cavity and converts X-rays to X-ray projection data about the oval cavity; a communication module for transmission of the projection data converted in the sensing unit; and a communication cable that is connected to the communication module.

Further, the communication cable of the intra-oral sensor is configured to transmit the projection data by being connected to a computing device such as a personal computer.

Further, the projection data is transmitted wirelessly through a Wi-Fi unit by connecting the communication cable of the intra-oral sensor to the Wi-Fi unit rather than to the computing device directly in a wired manner.

Meanwhile, in the conventional intra-oral sensor, high tension strength is imposed on the communication cable in accordance with movement of the intra-oral sensor when performing the intra-oral radiography, so there occurs a problem in that an electrical connection part between the sensing unit and the communication cable is damaged or the sensing unit and the communication cable are separated from each other, thereby causing communication interruption therebetween.

Further, since the conventional intra-oral sensor requires that the communication cable be frequently bent while using, cracks are caused in the conjunction part between the sensing unit and the communication cable, so there has been a problem of the sensing unit and the communication cable separating over time.

Further, when the number of intraoral radiographs is increased and when the tension strength for insertion into the oral cavity is increased, separation between the sensing unit and the communication cable increases, so there is a problem of reducing lifespan of the intra-oral sensor and requiring extra cost for purchasing an additional intra-oral sensor.

Further, the intra-oral sensor is for use on a plurality of patients so sterilization is a matter of importance. Generally, sterilization is implemented by cleaning or by using an additional sterilizing device so there is a problem of an increase in time and cost for sterilization.

Meanwhile, generally the projection data radiographed by the intra-oral sensor is displayed by being transmitted to a computer system of an operator through a picture archiving and communication system (PACS). In particular, when radiographing several small regions of several teeth in the oral cavity, there is a problem that it is difficult to distinguish whether stored projection data is data for an upper jaw or a lower jaw or to recognize which tooth is represented by the projection data.

DISCLOSURE

Technical Problem

The inventors have completed the invention by solving the above-mentioned problems of the communication cable connected to the sensing unit in the intra-oral sensor and by developing a configuration of the intra-oral sensor, the cradle, and the intra-oral sensing system, in which the intra-oral sensor has a more compact shape and is thereby easily positioned in the oral cavity.

Accordingly, another object of the present invention is to propose an intra-oral sensor, a cradle, and an intra-oral sensing system, in which the intra-oral sensor can transmit X-ray projection data without being connected to the computing device using additional communication cables.

Further, a further object of the present invention is to propose an intra-oral sensor, a cradle, and an intra-oral sensing system, in which the intra-oral sensor can perform transmission of projection data and can be charged with electricity at the same time.

Further, still another object of the present invention is to propose an intra-oral sensor, a cradle, and an intra-oral sensing system, in which the intra-oral sensor can perform transmission of projection data, can be charged with electricity, and can be sterilized at the same time.

Further, still another object of the present invention is to propose an intra-oral sensor, a cradle, and an intra-oral sensing system, which allows a user to easily recognize which part in a set of teeth is represented by image data corresponding to the projection data output from the cradle.

The objects of the present invention are not limited to the above-mentioned objects, and other unmentioned objects thereof will be clearly understood by those skilled in the art from the following descriptions.

Technical Solution

In order to achieve the above object, according to one aspect of the present invention, there is provided an intra-oral sensor that includes: a sensing unit converting X-rays to projection data; a memory storing the projection data therein; a data connector transmitting the projection data that is stored in the memory; a battery supplying driving power to the sensing unit and the memory; and a charging connector receiving electric power for charging the battery.

In a preferred embodiment, the intra-oral sensor further includes a casing containing the sensing unit, the memory, and the battery therein, and exposing the data connector and the charging connector to the outside.

Further, according to another aspect of the present invention, there is provided an intra-oral sensor including: a data connector transmitting a projection data and a charging connector receiving electric power for charging; and a cradle providing a mounting space to mount the intra-oral sensor therein, the cradle including: a data receiving terminal configured to transmit the projection data, and a charging terminal configured to supply the electric power, wherein the data receiving terminal is connected to the data connector and the charging terminal is connected to the charging connector while the intra-oral sensor is in the mounting space.

In a preferred embodiment, the cradle may include a sterilizer that is provided in the mounting space, and the sterilizing the intra-oral sensor when the intra-oral sensor is mounted in the cradle.

In a preferred embodiment, the sterilizer may be an ultraviolet lamp and may be turned on when the intra-oral sensor is mounted in the cradle.

In a preferred embodiment, the mounting space of the cradle may be provided with a plurality of slots for inserting the intra-oral sensor therein, and distinguishable from each other.

In a preferred embodiment, when the intra-oral sensor is mounted in one of the slots, the cradle may output the projection data of the mounted intra-oral sensor together with an identifier of the slot.

Further, the present invention may additionally provide only the cradle.

Advantageous Effects

The present invention has the following advantages.

First, in the intra-oral sensor according to the embodiment of the present invention, it is possible to implement a compact shape in which projection data converted in the sensing unit is stored in the memory so there is no need for provision of an additional communication module or an additional communication cable.

Further, when performing intraoral radiography for a patient, there is obtained an advantage that it is possible to easily position the intra-oral sensor in the oral cavity.

Further, in the intra-oral sensor according to the embodiment of the present invention, there is obtained an advantage that, since the intra-oral sensor includes the data connector and the charging connector that come into contact with an external device including the cradle, it is possible to perform transmission of the projection data and charging of the intra-oral sensor with electricity at the same time when mounting the intra-oral sensor in the external device including the cradle.

Further, in the intra-oral sensing system according to the embodiment of the present invention, transmission of the projection data and sterilization are performed at the same time by providing the sterilizer in the mounting space of the cradle, so it is possible to reduce time for sterilization.

Further, in the intra-oral sensing system according to the embodiment of the present invention, it is possible to easily recognize which part in a set of teeth is represented by image data corresponding to the projection data.

DESCRIPTION OF THE REFERENCE NUMERALS IN THE DRAWINGS

Figure 1:
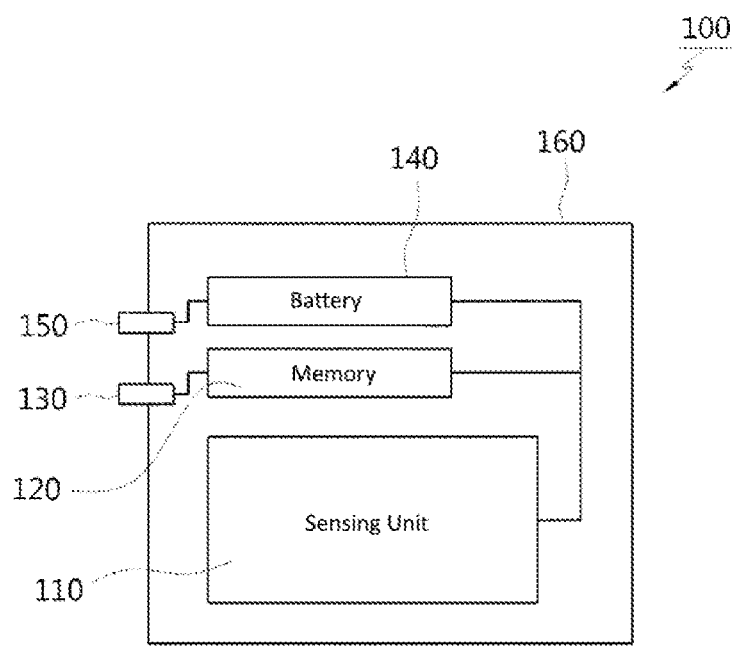
FIG. 1 is a block diagram schematically illustrating an intra-oral sensor according to an embodiment of the present invention.

110: sensing unit
120: memory
130: data connector
140: battery
150: charging connector
160: casing Best Mode Although terms used in the present invention are general terms that are widely used, these terms may be terms arbitrarily selected by the applicant in a specific case, and in this case, these terms should be interpreted as not the titles of the terms but the meaning described in the detailed description for implementing the invention or the meaning of the terms.

Hereinafter, a technical configuration of the present invention will be described in detail with reference to preferred embodiments illustrated in the accompanying drawings.

However, it should be understood that the present invention is not limited to the following embodiments and may be embodied in different ways. Wherever possible, the same reference numerals will be used throughout the drawings and the description to refer to the same or like parts.

Figure 2:
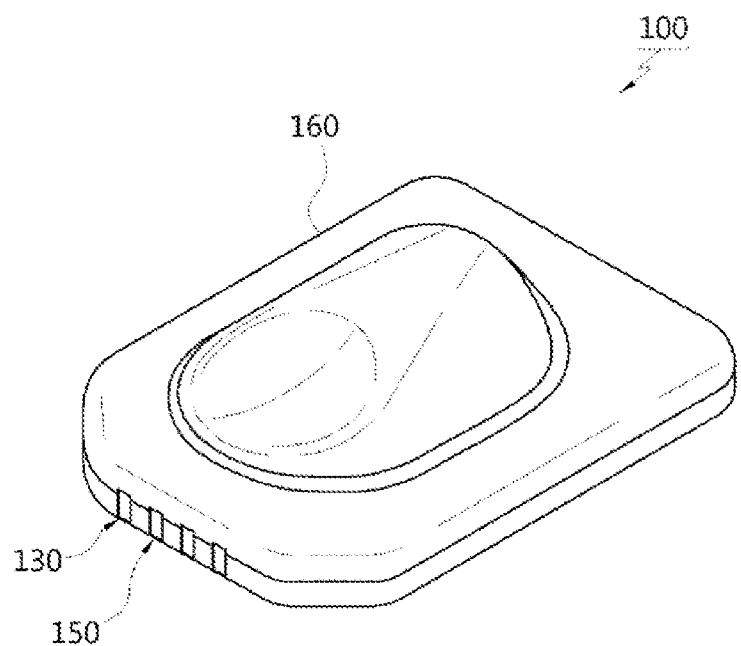
FIG. 2 is a view illustrating the intra-oral sensor according to the embodiment of the present invention.

FIG. 1 is a block diagram schematically illustrating an intra-oral sensor 100 according to an embodiment of the present invention, and FIG. 2 is a view illustrating the intra-oral sensor 100 according to the embodiment of the present invention.

Referring to FIGS. 1 to 2, the intra-oral sensor 100 according to the embodiment of the present invention is provided for obtaining X-ray projection data of the oral cavity of a patient by being used for intraoral radiography for the patient. The intra-oral sensor 100 is configured to be capable of transmission of data and to be charged by electricity using a cradle 200 when mounting the intra-oral sensor 100 in an external device having the cradle 200, and the intra-oral sensor 100 includes: a sensing unit 110, a memory 120, data connector 130, a battery 140, a charging connector 150, and a casing 160.

Here, the cradle 200 is provided for receiving the data from the intra-oral sensor 100 and charging of the intra-oral sensor 100 with electricity, and thus may be provided with a data receiving terminal 210 so as to receive the data and a charging terminal 220 to supply electric power for charging.

Further, the data receiving terminal 210 and the charging terminal 220 may be provided individually or may be provided as a single terminal having a function of transmission of data and charging with electricity.

Further, the cradle 200 may provide projection data transmitted from the intra-oral sensor 100 by being connected to a computing device 20 including a personal computer in a wired or wireless manner. To this end, the cradle 200 may contain a wireless communication module therein.

The sensing unit 110 is provided for converting X-rays projected from an external X-ray projection device to an electrical signal including the projection data. The sensing unit 110 may include an image sensor that generates the electrical signal from X-rays and a signal processing means that processes the electrical signal and generates the projection data, in which the image sensor may adapt an indirect conversion method using a scintillator or a direct conversion method using a photoconductive layer.

The memory 120 is provided for storage of the projection data and is electrically connected to the sensing unit 110, so the memory receives the electrical signal including the projection data from the sensing unit 110 and stores the electrical signal as data therein.

Further, the memory 120 may be provided as a memory device capable of storing and preserving the projection data converted in the sensing unit 110, such as, flash memory or random access memory (RAM).

Further, since the memory 120 is provided in the intra-oral sensor 100, the intra-oral sensor 100 can store and preserve the projection data even if the intra-oral sensor 100 is not provided with an additional communication cable. Thus, the intra-oral sensor 100 has a compact shape due to elimination of the communication cable and a communication module, thereby allowing easily positioning of the intra-oral sensor 100 in the oral cavity without interference of the communication cable during intraoral radiography of a patient.

The data connector 130 is provided for transmission of data with the external device including the cradle 200 and is electrically connected to the memory 120, so the data connector 130 transmits the projection data stored in the memory 120 to the external device including the cradle 200.

Further, when mounting the intra-oral sensor 100 in the cradle 200, the data connector 130 comes into contact with the data receiving terminal 210 of the cradle 200, so the data connector 130 transmits the projection data stored in the memory 120.

The battery 140 is provided for supply of driving power, particularly, driving power for operating the sensing unit 110, and when needed, the battery 140 may supply the driving power for operating the memory 120.

Further, the battery 140 is provided as a rechargeable battery, preferably the battery 140 is charged with electricity by receiving external power and supplies charged electric power as the driving power.

The charging connector 150 is provided for contact between the battery 140 and a means for external charging, so the battery 140 receives electric power for charging from outside. In other words, the charging connector 150 enables electrical connection between the battery 140 and the charging terminal 220 of the cradle 200.

Further, when mounting the intra-oral sensor 100 in the cradle 200, the charging connector 150 comes into contact with the charging terminal 220 of the cradle 200 so the charging connector 150 supplies the external power to the battery 140.

The casing 160 is provided for covering the sensing unit 110, the memory 120, and the battery 140 so as to prevent from exposure to the outside. The casing 160 protects against external shocks and impurities and prevents saliva of the patient from flowing into inside the casing 160 during intraoral radiography.

Further, the casing 160 may have a shape in which an upper casing 160 and a lower casing 160 are coupled to each other, and may be at least waterproofed.

The casing 160 has a structure in which the data connector 130 and the charging connector 150 are partially exposed to the outside, and may be further provided with an additional covering member (not shown) to cover the exposed parts of the data connector 130 and the charging connector 150.

Therefore, in the intra-oral sensor 100 according to the embodiment of the present invention, there is no need for provision of the communication cable for transmission of the obtained projection data so it is possible to easily position the intra-oral sensor 100 in the oral cavity and prevent risk of breakage of internal components due to tension strength of the communication cable.

Mode for Invention

Figure 3:
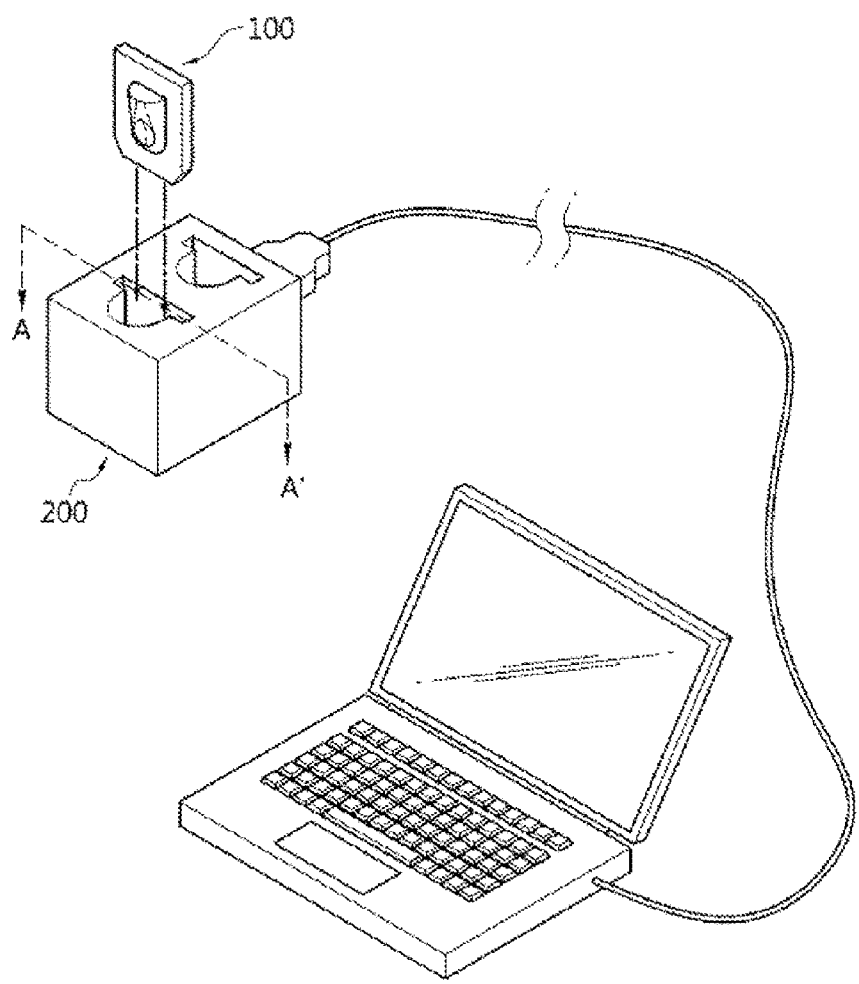
FIG. 3 is a view illustrating an intra-oral sensing system according to an embodiment of the present invention.
Figure 4:
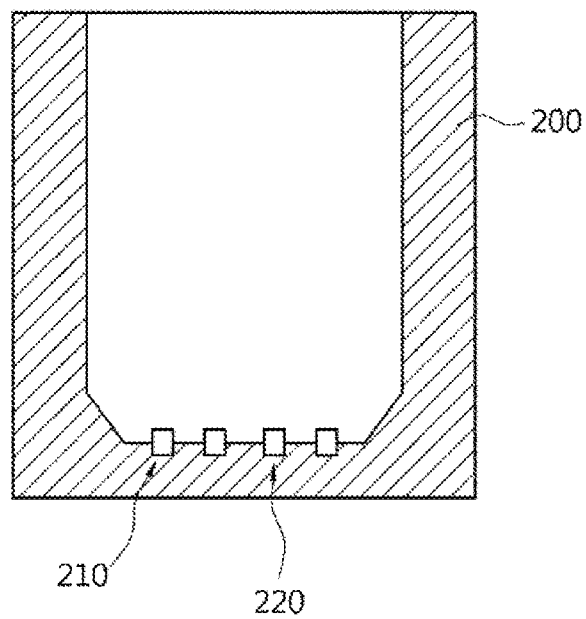
FIG. 4 is a view illustrating a cross-section taken along line A-A' of a cradle according to an embodiment of the present invention.

FIG. 3 is a view illustrating an intra-oral sensing system according to an embodiment of the present invention, and FIG. 4 is a view illustrating a cross-section taken along line A-A' of a cradle according to an embodiment of the present invention.

Referring to FIGS. 3 to 4, the intra-oral sensing system according to the embodiment of the present invention is configured to include the intra-oral sensor 100 and the cradle 200 where intra-oral sensor 100 is mounted therein.

Further, the intra-oral sensor 100 is provided to convert X-rays projected from the external projection device to the projection data so as to be stored in the memory 120 inside the intra-oral sensor 100, so there is no need for provision of the additional communication cable for transmission of data.

Substantially, the above-mentioned intra-oral sensor 100 is identical to the intra-oral sensor 100 according to the embodiment of the present invention, so a more detailed description will be omitted.

The cradle 200 may be provided with at least one mounting space 230 where the intra-oral sensor 100 is mounted therein, and may be provided with the data receiving terminal 210 receiving the projection data and the charging terminal 220 supplying the electric power for charging when mounting the intra-oral sensor 100 in the cradle 200. Here, the data receiving terminal 210 comes into contact with the data connector 130 of the intra-oral sensor 100, and the charging terminal 220 comes into contact with the charging connector 150 of the intra-oral sensor 100.

In other words, the cradle 200 is configured to receive the projection data stored in the intra-oral sensor 100 and charge the intra-oral sensor 100 with electricity at the same time. To this end, the cradle 200 may receive external power.

Further, the cradle 200 is connected to an external computing device, so when receiving the projection data from the intra-oral sensor 100, the cradle 200 supplies the projection data to the external computing device and supplies electric power received from the external computing device to the intra-oral sensor 100.

Figure 5:
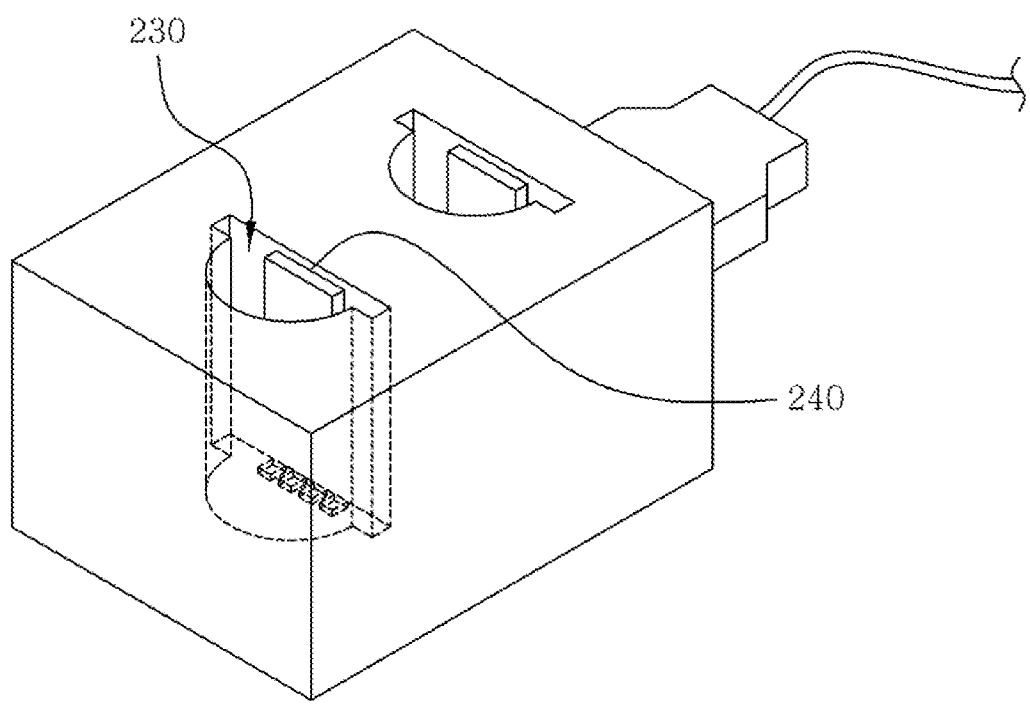
FIG. 5 is a view showing a sterilizer of the cradle according to an embodiment of the present invention.

Further, referring to FIG. 5, the cradle 200 may be further provided with a sterilizer 240 that sterilizes the intra-oral sensor 100 mounted in the mounting space 230 of the cradle 200.

Further, the sterilizer 240 performs sterilization by being turned on when the intra-oral sensor 100 is mounted in the cradle 200.

In other words, the intra-oral sensor 100 may be sterilized while at the same time transmitting the projection data or being charged with electricity. Thus, time and cost required for sterilization may be reduced.

Further, in the present invention, the sterilizer 240 is provided as an ultraviolet lamp. However, the sterilizer 240 may be substituted with any lamp capable of sterilization.

Further, FIG. 5 shows that one mounting space 230 is provided with one sterilizer 240. However, one mounting space 230 may be provided with a plurality of sterilizers 240, and a plurality of mounting spaces 230 may be provided with one sterilizer 240.

Further, the sterilizer 240 is provided inside the cradle 200 rather than being provided in the mounting space 230, and thus may project sterilization light in the mounting space 230.

Further, the cradle 200 may be provided additionally by being separated from the intra-oral sensing system.

Figure 6:
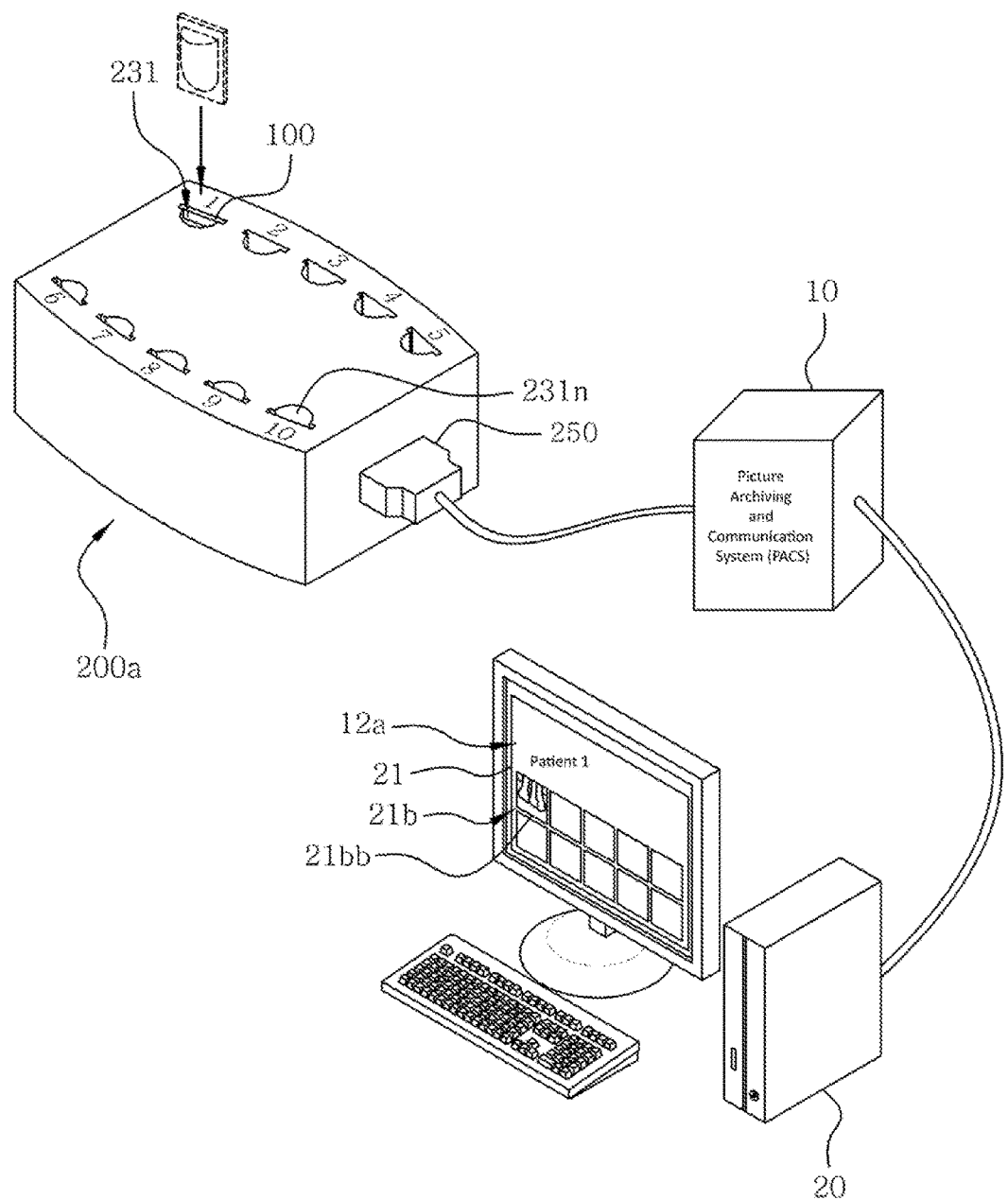
FIG. 6 is a view showing a cradle according to another embodiment of the present invention.

Further, FIG. 6 shows that another embodiment of the cradle 200, in which a cradle 200a according to another embodiment of the present invention is provided with a plurality of slots 231 and 231n where the intra-oral sensor 100 is mounted therein.

In other words, the cradle 200a according to another embodiment of the present invention is a cradle capable of simultaneously mounting a plurality of the intra-oral sensors 100 therein.

Further, the slots 231 and 231n are provided to be distinguishable from each other.

For example, the slots 231 and 231n may be provided as ten slots, and may be distinguished with numbers of a first slot 231 to a tenth slot 231n.

However, the number of the slots 231 and 231n is not be particularly limited.

Further, the slots 231 and 231n may be distinguished with various identifiers such as not only figures but also letters or symbols or images, etc.

Further, the slots 231 and 231n output their own identifiers together with the projection data when the projection data is output from intra-oral sensor 100 loaded in the slot.

As a result, the projection data output from data output terminal 250 of the cradle 200a includes an identifier of a slot.

Likewise, the reason why the projection data including the identifier of the slot is output from the intra-oral sensor 100 is because the intra-oral sensor 100 obtains image data of only a local area of the teeth so as to recognize which part in a set of teeth is represented by the image data corresponding to the obtained projection data.

For example, the first to fifth slots out of ten slots may be used for receiving projection data of an upper jaw, and sixth to tenth slots may be used for receiving projection data of a lower jaw.

Further, a first slot may be used for receiving projection data of a molar area of a right upper jaw, a fifth slot may be used for receiving projection data of a molar area of a left upper jaw, a sixth slot may be used for receiving projection data of a molar area of a right lower jaw, and a tenth slot may be used for receiving projection data of a molar area of a left lower jaw.

In other words, when an operator performs intraoral radiography on the molar area of the right upper jaw of the patient using the intra-oral sensor 100 and then inserts the intra-oral sensor 100 into the first slot, the projection data of the molar area of the right upper jaw and the identifier of the first slot are output together through the data output terminal 230.

Meanwhile, the projection data output from the cradle 200a is typically transmitted to a computer system 20 of the operator through a picture archiving and communication system (PACS) 10, so the projection data is displayed in the form of an electronic dental chart 21.

Further, the electronic dental chart 21 is provided with a patient information output section 21a where patient information is output thereto and a teeth image output section 21b where the teeth image of the patient is output thereto, in which the teeth image output section 21b is provided with a plurality of partial teeth image output sections 21bb where the partial teeth image of the patient is output thereto.

In other words, in the case that the projection data is data input into the first slot, the projection data is brought to be output to a section 21bb for displaying the molar area of the right upper jaw in the partial teeth image output sections 21bb. Thus, the operator can easily recognize which part in a set of teeth of the patient is represented by projection data corresponding to the projection data output to the section 21bb.

Further, a process of transmitting the projection data of a radiography subject to the computing device will be briefly described by using the intra-oral sensing system according to the present invention. First, when not in use, the intra-oral sensor 100 is charged by being input electric power that is transmitted from the computing device through the cradle 200 while being mounted in the cradle 200.

Next, when performing intraoral radiography on the radiography subject, the operator separates the intra-oral sensor 100 from the cradle 200 and inserts the sensor 100 into the subject's oral cavity, and then projects X-rays onto the intra-oral sensor 100 in the oral cavity of the radiography subject by using the external X-ray projection device, whereby the intra-oral sensor 100 generates projection data from X-rays and stores the projection data.

Here, intraoral radiography on the radiography subject may be performed plural times so the intra-oral sensor 100 stores all of a plurality of the projection data, and the intra-oral sensor 100 is not provided with the additional communication and power cables so the intra-oral sensor 100 may be easily positioned inside the oral cavity of the radiography subject.

Next, when removing the intra-oral sensor 100 from the oral cavity of the radiography subject and mounting it in the cradle 200, the projection data stored in the intra-oral sensor 100 is transmitted to the computing device 20 through the cradle 200 and the intra-oral sensor 100 is simultaneously charged with electricity. At the same time, the intra-oral sensor 100 is sterilized by the sterilizer 240.

In other words, there is an advantage in that the intra-oral sensor 100 performs charging of electricity and transmission of the projection data at the same time through a simple process of mounting the intra-oral sensor 100 in the cradle 200.

Next, the operator can recognize information about teeth in the oral cavity of the radiography subject through corresponding projection data that is transmitted to the computing device 20.

Further, the projection data output from the cradle 200 may be transmitted to the computing device 20 of the operator through the picture archiving and communication system (PACS).

Further, in the computing device 20, when the projection data input to the computing device 20 includes the identifier of the slot, the computing device 2 outputs the projection data that is input to the teeth image data output section 21b corresponding to the identifier of the slot in the teeth image data output section 21*b* of the electronic dental chart 21.

Therefore, the operator can easily recognize which part in a set of teeth is represented by the projection data input to the computing device 20.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention can be used for an apparatus for obtaining a medical radiography image data, more particularly, for an apparatus for obtaining a dental radiography image data.

The invention claimed is:

1. An intra-oral sensing system, comprising:
    an intra-oral sensor including a data connector transmitting projection data and a charging connector receiving electric power for charging; and
    a cradle providing a mounting space to mount the intra-oral sensor therein, the cradle including: a data receiving terminal configured to transmit the projection data, a charging terminal configured to supply the electric power, and a sterilizer sterilizing the intra-oral sensor wherein the data receiving terminal is connected to the data connector and the charging terminal is connected to the charging connector while the intra-oral sensor is in the mounting space.

2. The intra-oral sensing system of claim 1, wherein
    the sterilizer is provided in the mounting space, and sterilizing the intra-oral sensor when the intra-oral sensor is mounted in the cradle.

3. The intra-oral sensing system of claim 2, wherein
    the sterilizer is an ultraviolet lamp, and is turned on when the intra-oral sensor is mounted in the cradle.

4. The intra-oral sensing system of claim 1, wherein the mounting space of the cradle is provided with a plurality of slots for inserting the intra-oral sensor therein, and distinguishable from each other.

5. The intra-oral sensing system of claim 4, wherein, when the intra-oral sensor is mounted in one of the slots, the cradle outputs the projection data of the mounted intra-oral sensor together with an identifier of the slot.

* * * * *